United States Patent
Ferek-Petric

(12) 
(10) Patent No.: US 6,442,430 B1
(45) Date of Patent: Aug. 27, 2002

(54) IMPLANTABLE MEDICAL DEVICE PROGRAMMERS HAVING HEADSET VIDEO AND METHODS OF USING SAME

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/727,463

(22) Filed: Dec. 4, 2000

(51) Int. Cl.$^7$ ................................................ A61N 1/37
(52) U.S. Cl. ...................................................... 607/32
(58) Field of Search ............................. 607/30, 31, 32, 607/60

(56) References Cited

U.S. PATENT DOCUMENTS

| | | |
|---|---|---|
| 4,316,472 A | 2/1982 | Mirowski et al. |
| 4,375,817 A | 3/1983 | Engle et al. |
| 4,379,459 A | 4/1983 | Stein |

(List continued on next page.)

FOREIGN PATENT DOCUMENTS

WO    WO92/18198    10/1992

OTHER PUBLICATIONS

Arzbaecher et al., "Automatic Tachycardia Recognition", *PACE*, 541–547 (May–Jun. 1984).
Olson et al., "IEEE Computer Society Press", *Computers in Cardiology*, 167–170 (Oct. 7–10, 1986.)

Primary Examiner—Scott M. Getzow
(74) Attorney, Agent, or Firm—Thomas F. Woods; Eric R. Waldkoetter; Thomas G. Berry

(57) ABSTRACT

Programmers, systems and methods utilizing body-wearable components, such as a head-mounted video display apparatus, are provided to program implantable medical devices (IMDs). The head-mounted video display apparatus provides information regarding programming parameters as well as information regarding the patient and/or the IMD. By being worn on the body, programmers of the present invention are highly portable. Further, by providing a head-mounted video display apparatus, programmers of the present invention provide a display that remains viewable even in crowded environments.

35 Claims, 8 Drawing Sheets

U.S. PATENT DOCUMENTS

| | | | |
|---|---|---|---|
| 4,384,585 A | 5/1983 | Zipes | |
| 4,476,868 A | 10/1984 | Thompson | |
| 4,556,063 A | 12/1985 | Thompson et al. | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallock | |
| 4,800,883 A | 1/1989 | Winstrom | |
| 4,821,723 A | 4/1989 | Baker, Jr. et al. | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,099,838 A | 3/1992 | Bardy | |
| 5,117,824 A | 6/1992 | Keimel et al. | |
| 5,131,388 A | 7/1992 | Pless | |
| 5,144,949 A | 9/1992 | Olson | |
| 5,158,078 A | 10/1992 | Bennett et al. | |
| 5,163,427 A | 11/1992 | Keimel | |
| 5,188,105 A | 2/1993 | Keimel | |
| 5,199,428 A | 4/1993 | Obel et al. | |
| 5,207,218 A | 5/1993 | Carpentier et al. | |
| 5,269,298 A | 12/1993 | Adams | |
| 5,312,453 A | 5/1994 | Shelton | |
| 5,314,430 A | 5/1994 | Bardy | |
| 5,330,507 A | 7/1994 | Schwartz | |
| 5,331,966 A | 7/1994 | Bennett et al. | |
| 5,354,186 A | 10/1994 | Wyborny et al. | |
| 5,354,316 A | 10/1994 | Keimel | |
| 5,545,186 A | 8/1996 | Olson et al. | |
| D385,855 S | 11/1997 | Ronzani | |
| 5,690,686 A | 11/1997 | Min et al. | |
| 387,898 A | 12/1997 | Ronzani | |
| 5,719,743 A | 2/1998 | Jenkins et al. | |
| 5,719,744 A | 2/1998 | Jenkins et al. | |
| 5,724,985 A | * 3/1998 | Snell et al. | |
| 5,752,976 A | 5/1998 | Duffin et al. | |
| 5,757,339 A | 5/1998 | Williams et al. | |
| 5,800,465 A | 9/1998 | Thompson et al. | |
| D390,552 S | 12/1998 | Ronzani | |
| 5,844,656 A | 12/1998 | Ronzani et al. | |
| 5,844,824 A | 12/1998 | Newman et al. | |
| D411,179 S | 6/1999 | Toyosata | |
| 5,948,047 A | 9/1999 | Jenkins et al. | |
| 6,057,758 A | * 5/2000 | Dempsey et al. | |

* cited by examiner

IMPLANTABLE MEDICAL DEVICE PROGRAMMERS HAVING HEADSET VIDEO AND METHODS OF USING SAME

FIELD OF THE INVENTION

The present invention relates to implantable medical devices such as cardiac pacemakers and defibrillators. More particularly, the present invention pertains to implantable medical device programmers having a headset video monitor and methods for their use.

BACKGROUND

A wide variety of implantable medical devices (IMDs) are known and commercially available. Generally, these devices utilize a bio-compatible case having a connector block mounted thereto. The connector block includes receptacles for leads that may be used for electrical stimulation and/or for sensing physiological activity. For example, an implantable cardiac device, e.g., an implantable pacemaker-cardioverter-defibrillator (PCD), may use such leads to monitor activity of a human heart and to deliver therapy thereto in the event undesirable heart activity is detected.

IMDs typically require programming by a physician or medical technician to ensure that the therapy delivered by the IMD corresponds to the specific treatment required by the patient. In modern IMDs, programming is typically accomplished via an external programming apparatus that consists of an integrated computer system incorporating the IMD programming electronics and appropriate programming software, a keyboard for data entry, and a video monitor for viewing relevant programming parameters. During operation, a telemetry module, e.g., a programming wand, tethered to the computer system is held near the patient in close proximity to the implanted medical device. Using wireless communication protocols, e.g., bi-directional RF, the telemetry module permits transmission of programming instructions to and reception of status information from the IMD. The physician monitors this information on the video monitor and controls programming functions via the system keyboard.

While effective, these programmers have drawbacks. For instance, because they are somewhat large and typically require a relatively flat and stable surface on which to operate, they are normally operated from atop a wheeled cart or a fixed desk. The cart is particularly advantageous because it allows the programmer, which may weigh upwards of several pounds, to be quickly and easily moved to and from the patient's bedside.

Although the cart is beneficial for transporting the programmer, space proximate the patient is limited in crowded medical environments. Accordingly, if placed adjacent the patient, the cart/programmer may displace other equipment and/or interfere with the movement of medical personnel.

As a result, the cart is often placed in a more peripheral location, e.g., away from the patient. While such placement reduces cart interference, it also results in inconvenient orientation of the video monitor and the keyboard. For instance, when the programmer is remotely positioned, the video monitor is typically oriented so that the physician is unable to conveniently observe both the monitor and the patient. This is undesirable as some portions of the programming operation require, or at least benefit from, visual contact with the patient. In addition, remote positioning of the programmer undesirably allows medical personnel to inadvertently block the physician's view of the monitor.

U.S. Pat. No. 5,752,976 to Duffin et al. discloses a telemetry system that includes an external patient communications control device either worn by or located in proximity to the patient. In other embodiments, Duffin et al. discloses use of a global positioning system (GPS) to locate remote patients. While effective for remotely monitoring and programming a patient's IMD, Duffin et al. does not specifically address the problems discussed above, e.g., poor monitor/programmer placement relative to the patient, difficulties during programming.

Various body-worn computers are also known in the art. For example, U.S. Pat. No. 5,948,047 to Jenkins et al. discloses a body-wearable mobile computer having a keyboard 24 and display 25 (see Jenkins et al., FIG. 4). Similarly, U.S. Pat. No. 5,844,824 to Newman et al. discloses a body-worn, hands-free computer system having a computer unit 106 and a video display 110 (see Newman et al., FIG. 1). However, none of these computer systems address the unique needs of IMD programmers.

Accordingly, systems for programming IMDs are known as are systems for transmitting IMD status or patient status/location to remote facilities. These systems are described above and in the documents listed in Table 1 below. Table 1 further includes documents directed to body-wearable computer systems.

TABLE 1

| Patent No. | Inventor | Issue Date |
|---|---|---|
| 5,752,976 | Duffin, et al. | May 19, 1998 |
| 5,948,047 | Jenkins et al. | Sep. 07, 1999 |
| 5,844,656 | Ronzani et al. | Dec. 01, 1998 |
| 5,844,824 | Newman et al. | Dec. 01, 1998 |
| 5,757,339 | Williams et al. | May 26, 1998 |
| 5,719,744 | Jenkins et al. | Feb. 17, 1998 |
| 5,719,743 | Jenkins et al. | Feb. 17, 1998 |
| D411,179 | Toyosato | Jun. 22, 1999 |
| D390,552 | Ronzani | Feb. 10, 1998 |
| D387,898 | Ronzani | Dec. 23, 1997 |
| D385,855 | Ronzani | Nov. 4, 1997 |

All documents listed in Table 1 herein above are hereby incorporated by reference in their respective entireties. As those of ordinary skill in the art will appreciate readily upon reading the Summary of the Invention, Detailed Description of the Embodiments, and claims set forth below, many of the devices and methods disclosed in the documents of Table 1 and others documents incorporated by reference herein may be modified advantageously by using the teachings of the present invention.

SUMMARY OF THE INVENTION

The present invention has certain objects. That is, various embodiments of the present invention provide solutions to one or more problems existing in the art with respect to IMD programming apparatus and techniques. One such problem involves the need to position the programming apparatus proximate the patient without impeding the movement of medical personnel. Other problems, for example, include: providing adequate and generally unimpeded visibility for the physician operating the programmer; and physically locating the programmer in the crowded area near the patient's bedside.

In comparison to known techniques for programming IMDs, various embodiments of the present invention may provide one or more of the following advantages. For instance, the programmer may remain generally attached to the physician so that no additional space proximate the patient is required. Further, a display for providing information to the physician regarding the programmer and/or patient may be body-wearable, e.g., a headset mounted video display apparatus, permitting generally unencumbered line of sight for the physician. By providing some of all of the programmer components as body-wearable devices, programmers and methods of the present invention avoid interfering with other equipment and/or personnel surrounding the patient.

Some embodiments of the present invention provide one or more of the following features. For example, some embodiments provide a programmer for programming an implantable medical device where the programmer may include programming circuitry and a body-wearable video display apparatus coupled to the programming circuitry. The video display apparatus may be operable under the control of the programming circuitry to display at least programming information concerning the implantable medical device. The video display apparatus may be a microdisplay attached to a headset. A data entry device coupled to the programming circuitry may also be included as may a telemetry apparatus operable under control of the programming circuitry to communicate with the implantable medical device. The data entry device may include a keyboard, trackball, and/or a microphone and may further be integral with a housing enclosing the programming circuitry or may be separate from the housing. In some embodiments, the telemetry apparatus includes a programming wand while other embodiments may include an antenna in lieu thereof or in addition to the wand.

In comparison to known techniques for programming an implantable medical device, various embodiments of the present invention may provide one or more of the following features: providing an implantable medical device having an implantable medical device telemetry receiver; and providing a programming apparatus. The programming apparatus may include programming circuitry; a body-wearable video display apparatus coupled to the programming circuitry (where the video display apparatus is operable under control of the programming circuitry to display at least programming information associated with the implantable medical device); a data entry device coupled to the programming circuitry; and a telemetry apparatus operable under control of the programming circuitry to communicate with the implantable medical device. Techniques in accordance with the present invention may further include programming the implantable medical device with the programming apparatus, wherein programming information is displayed on the video display apparatus. Programming the implantable medical device may further include, for example: transmitting programming instructions from the telemetry transmitter to the implantable medical device telemetry receiver; and entering programming instructions from a data entry device coupled to the programming circuitry. In some embodiments, entering programming instructions may include: typing keystrokes on a keyboard; manipulating a trackball; and/or providing voice commands to a microphone.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
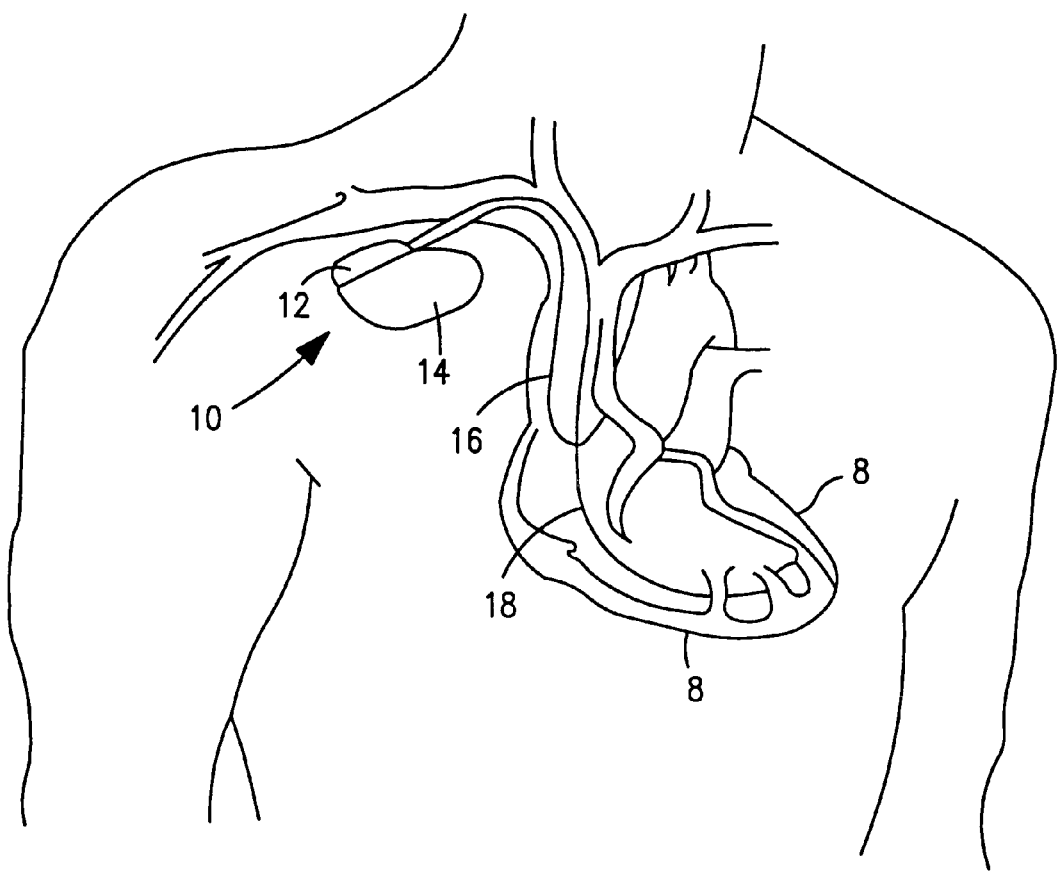
FIG. 1 is an implantable medical device (IMD) in accordance with one embodiment of the invention, wherein the IMD is shown implanted within the body of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and re-polarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
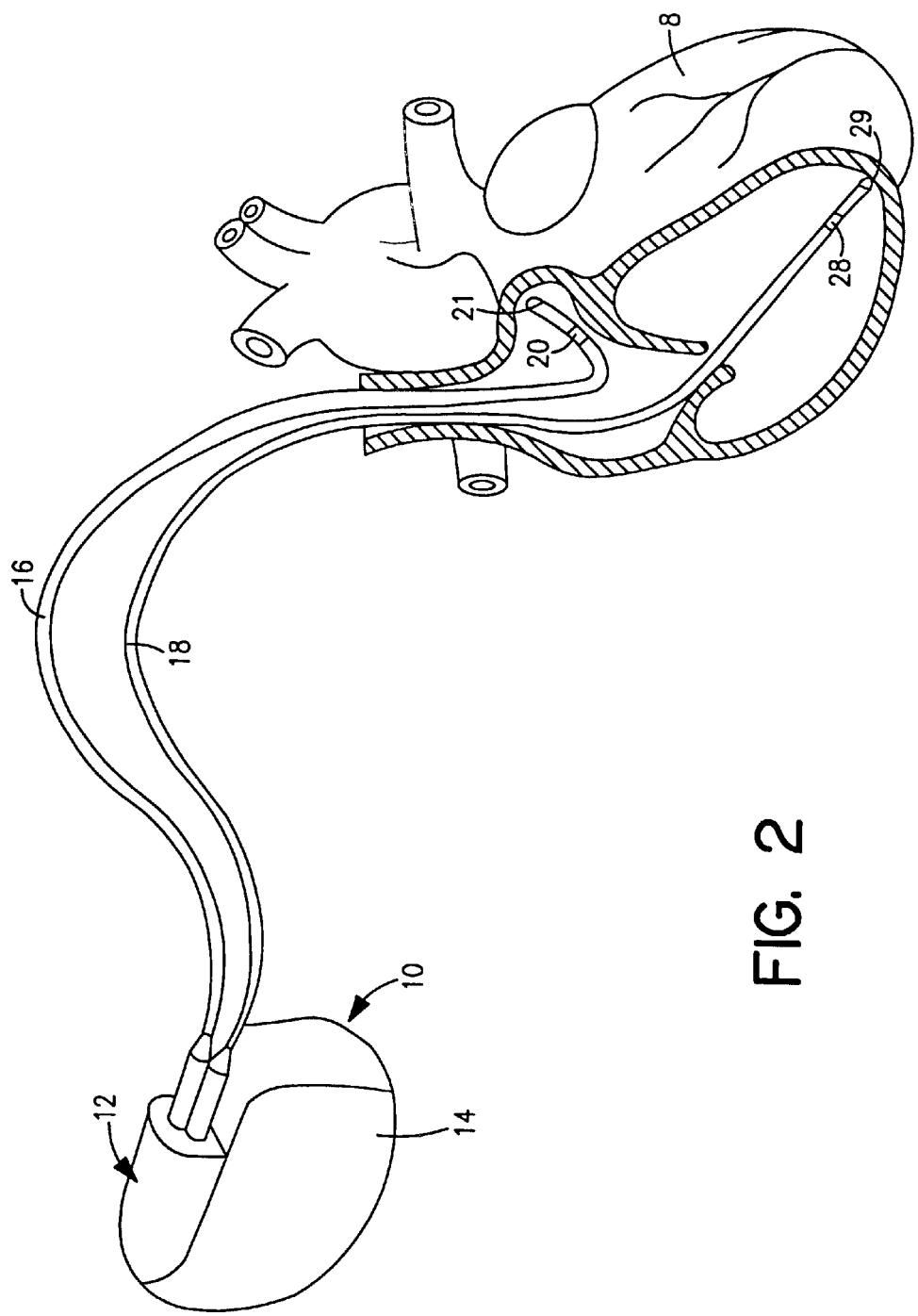
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
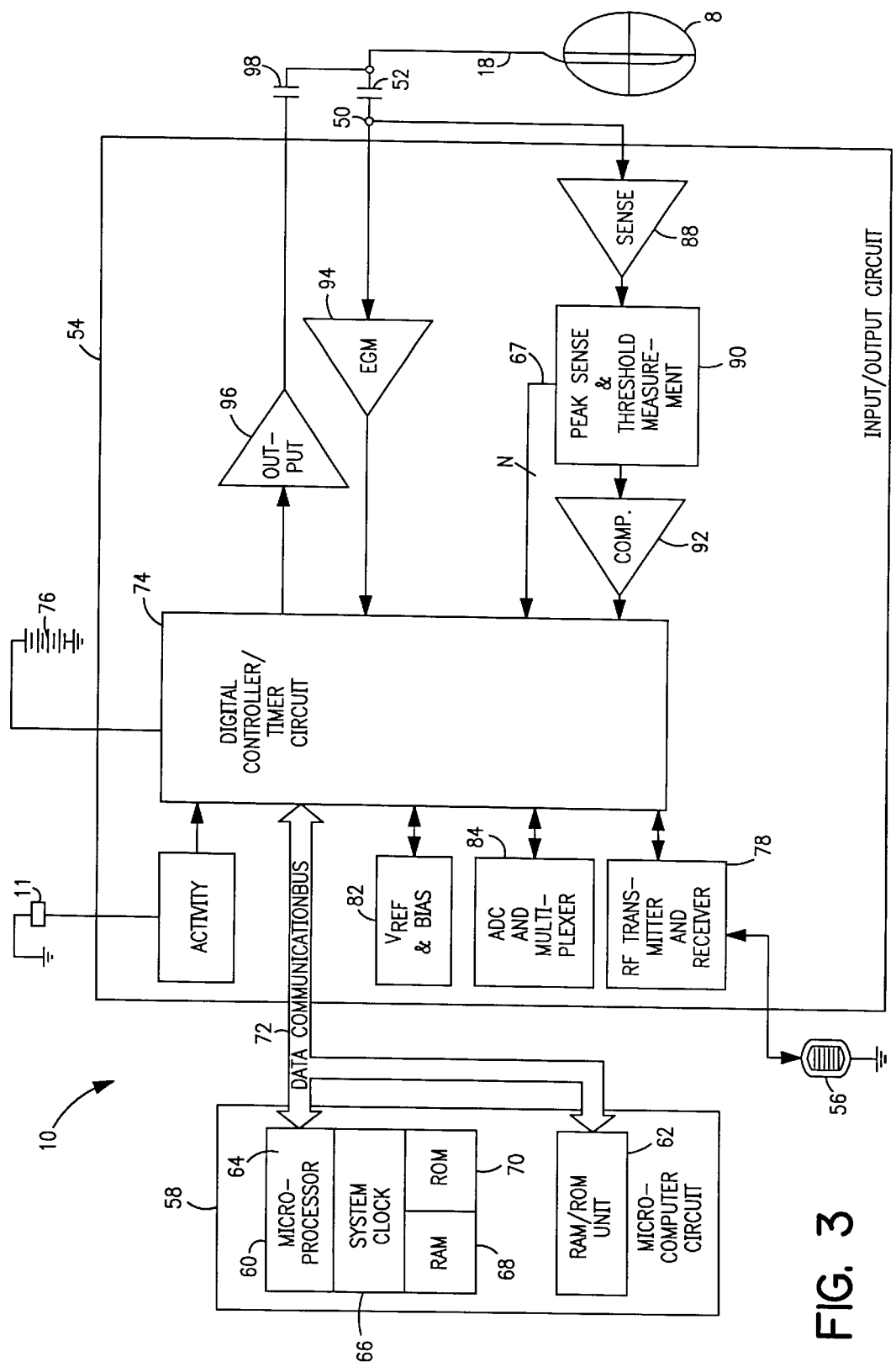
FIG. 3 is a functional block diagram of an IMD in accordance with one embodiment of the present invention where the IMD is a pacemaker.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is preferably programmable by means of a programming unit according to the present invention as described further below. Other programmers may also be used. One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, inpuy/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate-responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Further, the present invention is not limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
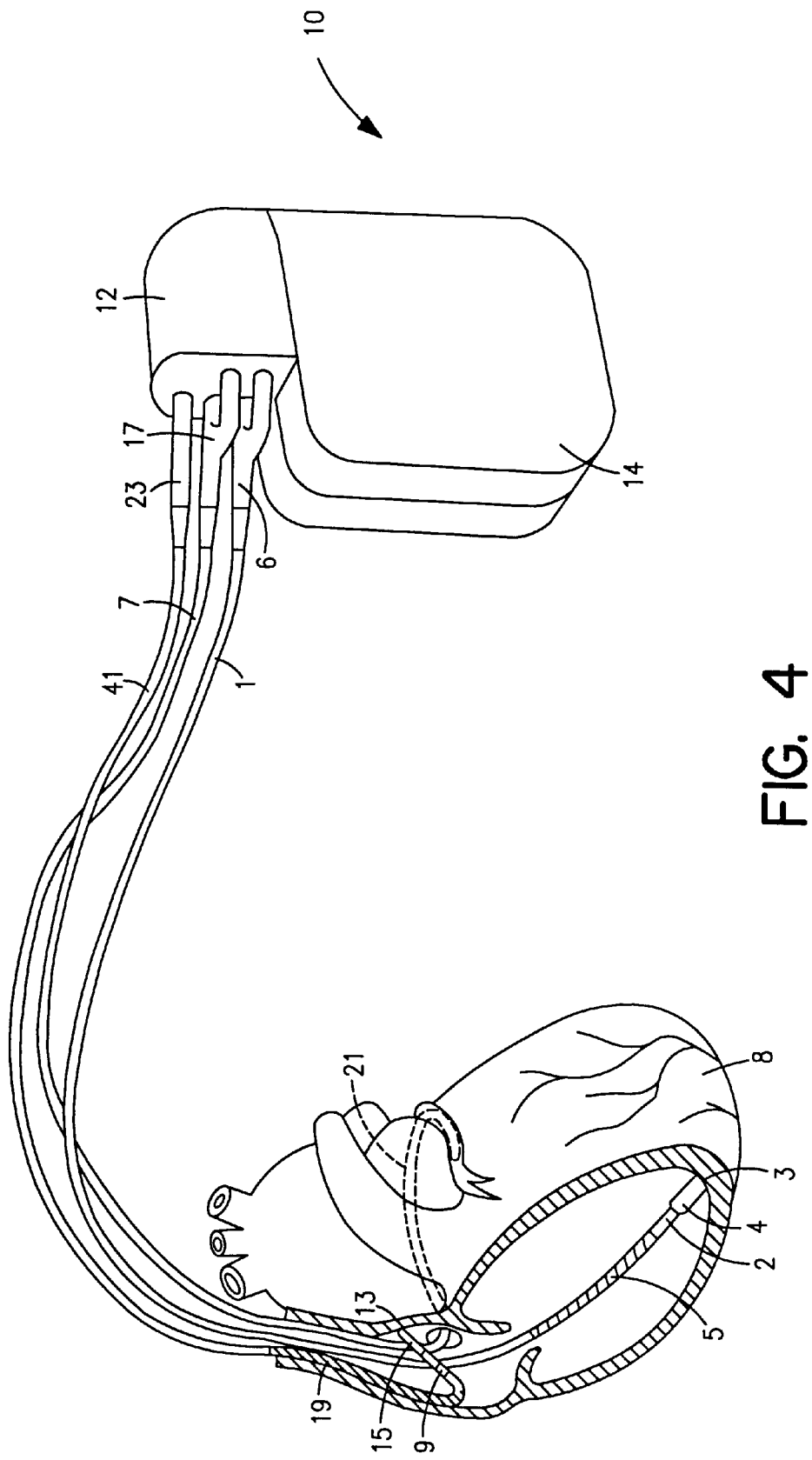
FIG. 4 is an IMD in accordance with another embodiment of the invention, wherein the IMD is an implantable pacemaker-cardioverter-defibrillator (PCD)
Figure 5:
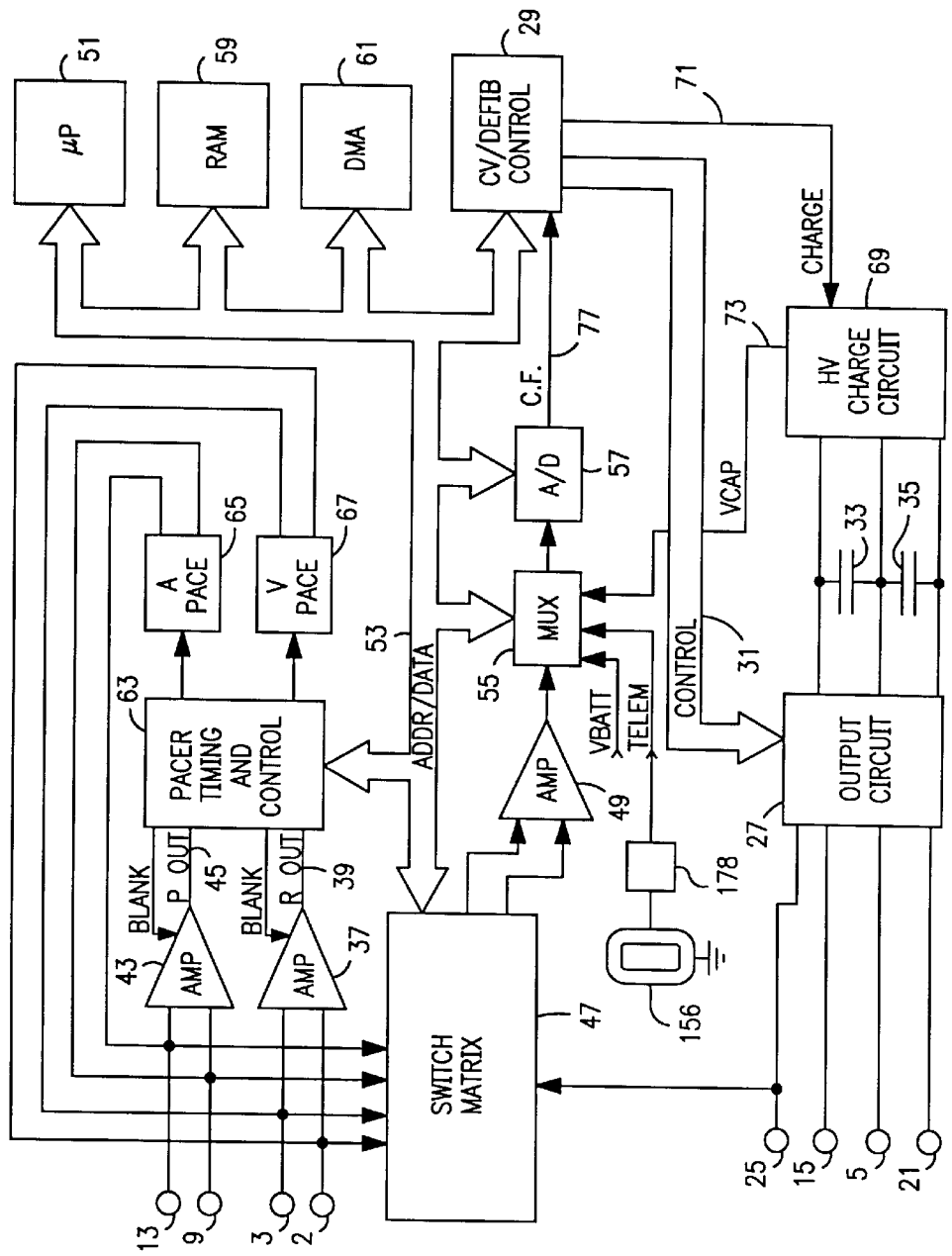
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known in the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

Like the pacemaker IMD illustrated in FIG. 3, the PCD of FIG. 5 also includes RF transmitter and receiver telemetry unit 178 coupled to antenna 156 to permit communication with the programmer as described herein.

An example of circuitry which may be used to control delivery of monophasic pulses is disclosed in U.S. Pat. No. 5,163,427 to Keimel. Output control circuitry similar to that disclosed in the above cited patent issued to Mehra et al. or U.S. Pat. No. 4,800,883 to Winstrom, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennett et al. The present invention is believed to find wide application to any form of implantable electrical device.

Various embodiments of IMD 10 are described above. Attention is now directed to programmers, programming systems, and methods for programming such IMDs in accordance with the present invention.

Figure 6:
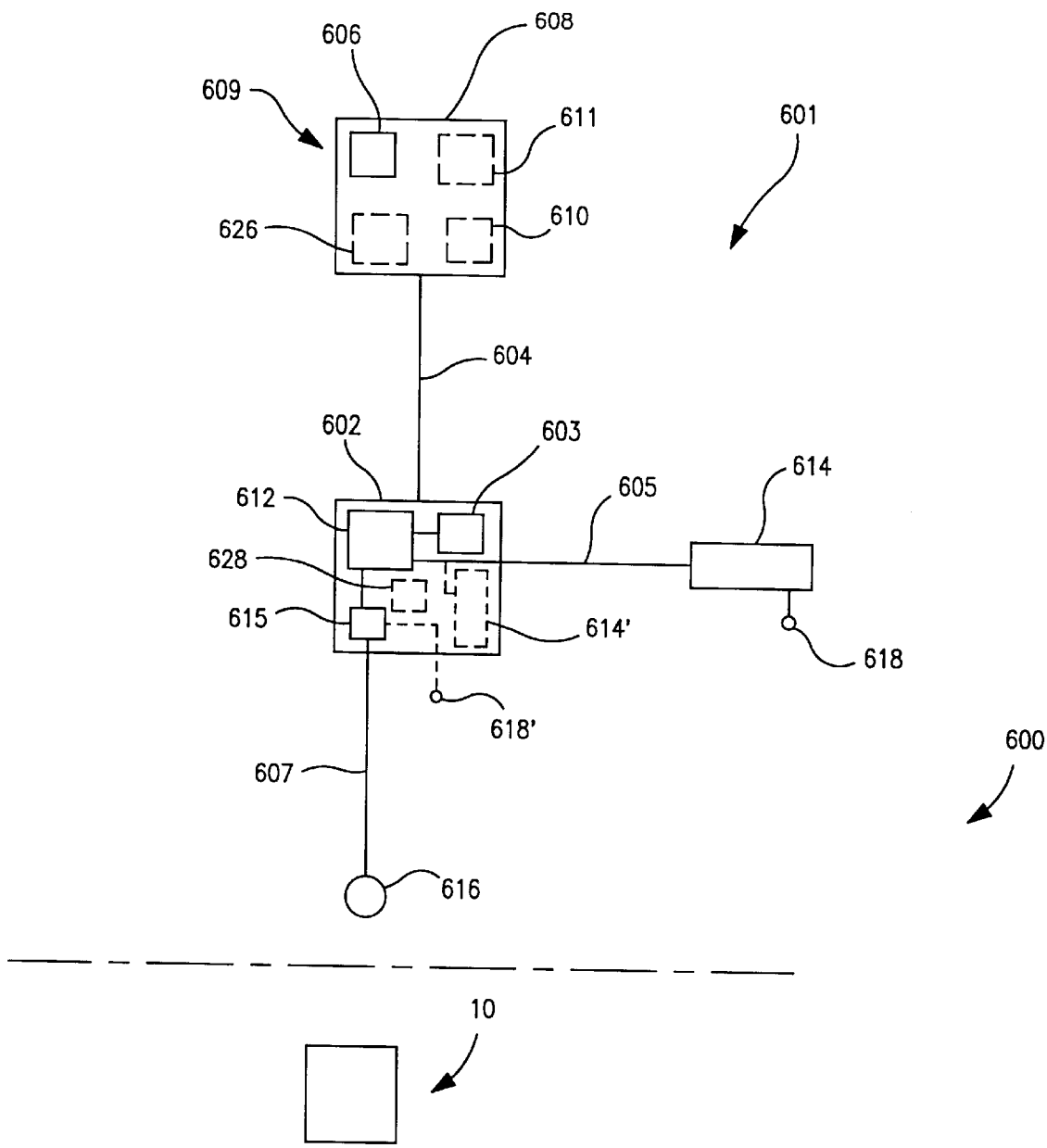
FIG. 6 is a functional block diagram of a programming system in accordance with one embodiment of the invention.

FIG. 6 diagrammatically illustrates a programming system 600 for programming IMD 10 in accordance with one embodiment of the invention. System 600 may include a programmer or programming apparatus 601 and IMD 10. Programmer 601 preferably includes a housing 602 which, in one embodiment, is body-wearable, e.g., securable around the waist. Housing 602 may enclose programming circuitry 612 which operatively controls programmer 601 during operation. Housing 602 may also include a power supply, e.g., rechargeable battery source 603, to power programmer 601. For the sake of clarity, the electrical coupling of the various components is not fully illustrated in FIG. 6.

Figure 7:
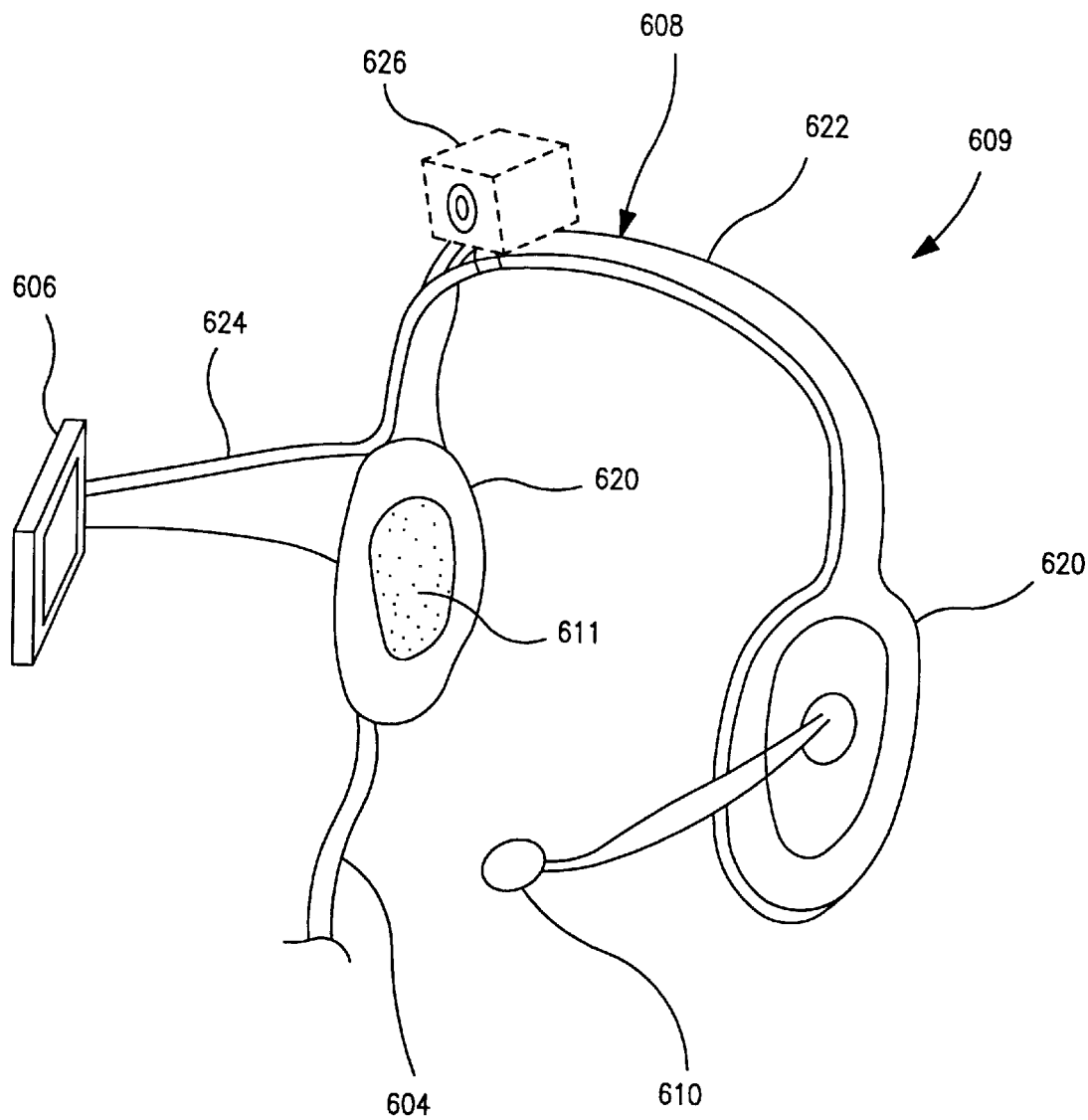
FIG. 7 is a perspective view of a headset apparatus in accordance with one embodiment of the invention.

A body-wearable video display apparatus 606 may be coupled to housing 602 by cable 604. While video display apparatus 606 may be worn on the body in most any fashion which permits the display to remain visible, e.g., on the cuff of the arm, the embodiments described and illustrated herein preferably secure video display apparatus 606 to the operator's head with a headset 608 (see FIG. 7). Headset 608 may, for purposes further described below, also incorporate an input device, e.g., microphone 610 and a secondary output device, e.g., speaker 611. Other peripheral devices (not shown), e.g., printers, recorders, and, as shown in FIGS. 6 and 7, a video camera 626 (further described below), may also be included with programmer 601. These other peripheral devices may be incorporated into or otherwise attached to headset 608. Alternatively, these devices, which may also be body-wearable, may couple to programmer 601 elsewhere, e.g., at housing 602. For simplicity, the combined headset 608, display 606, optional input and output devices and any headset peripheral devices are collectively referred to hereinafter as "headset apparatus 609."

Also preferably coupled to housing 602 by cable 605 is data input device 614. While shown as a separate component, input device 614 may, in another embodiment, be integral with housing 602 (see reference 614' in FIG. 6). Data input device 614 may allow the operator to control programming circuitry 612. For instance, device 614 may be a keyboard, similar in most respects to a conventional computer keyboard, which allows manipulation of programming circuitry and other system functions via keystrokes. Alternatively, device 614 may be a trackball, which, in conjunction with visual cues provided on display 606, permits manipulation of programming circuitry 612.

In one embodiment, programmer 601 incorporates a graphical user interface (GUI) such as the icon-based "Vision" software produced by Medtronic, Inc. of Minneapolis, Minn. Such GUIs may preferably be IMD-specific to present at least programming information to the user. Nonetheless, a non-specific GUI, e.g., Microsoft "Windows," may also be provided. Programming information, as used herein, generally refers to any information beneficial to the programming process, e.g., instructions, IMD status information, patient status data (e.g., ECG), etc.

Programmer 601 may further include a telemetry apparatus 615 permitting uni-directional or, more preferably, bi-directional communication with RF transmitter and receiver telemetry unit 78 (see FIG. 3) or 178 (see FIG. 5) of IMD 10. In one embodiment, telemetry apparatus 615 includes a wand 616 tethered to housing 602 by cable 607. Housing 602 may optionally include a holder (not shown) for receiving wand 616 when not in use (a similar holder may be provided to hold input device 614 and headset apparatus 609). Using standard communication protocols, e.g., RF, wand 616 may communicate with, e.g., send programming instructions to and receive IMD/patient status information from, IMD 10. An example of a device using such standard communication protocols is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from IMD 10.

Where telemetry apparatus 615 has appropriate range capability, wand 616 may be replaced with a telemetry antenna 618 electrically coupled to telemetry apparatus 615, e.g., transmitter and receiver circuitry, and mechanically attached to one or both of input device 614 and housing 602 (See reference 618').

While the components of programmer 601 are illustrated and described as interconnected by cables 604, 605, and 607, other embodiments may utilize wireless protocols, e.g., RF, to communicate therebetween. In this case, each component, e.g., housing 602, input device 614, headset apparatus 609, and wand 616, may communicate either directly or indirectly with one another.

FIG. 7 is a perspective view of an exemplary headset apparatus 609. Headset 608 preferably includes one or more earpieces 620 interconnected by a band 622. Earpieces 620 may, as described above, include optional speakers 611, microphone 610 and video camera 626. Video display apparatus 606 may be coupled to headset 608 by an adjustable arm 624 which supports the display 606 in front of the operator's head. Display 606 is preferably a microdisplay. A microdisplay is a small lightweight display that is capable of emulating a much larger, conventionally-sized display. In one embodiment, for example, the video display apparatus is similar to that used on the Xybernaut MA IV model computer produced by Xybernaut Corp. of Fairfax, Va. The Xybernaut MA IV uses a microdisplay having a diagonal dimension of approximately one inch yet emulates a larger, e.g., 15", monitor.

Embodiments that utilize video camera 626 may permit a technician or physician to program the IMD while being monitored by a remote physician stationed at a remote location. For instance, video camera 626 may be coupled to a wireless computer network circuit 628 preferably located within housing 602 as shown in FIG. 6. Camera 626 and circuit 628 enable remote visual communication with the technician and patient, e.g., camera 626 and circuit 628 permit capture of video data and transmission of same to the remote physician. The remote physician may then "see" the bedside of the patient and preferably communicate with the programming technician via speaker 611 and microphone 610. Examples of systems that permit remote communication are discussed in assignee's copending U.S. patent application Ser. No. 09/348,506, entitled "System for Remote Communication with a Medical Device" and filed Jul. 07, 1999.

Camera 626 may be directed towards the patient or, optionally, towards display 606. Alternatively, the video signal may be devoted to patient observation while the display information is transmitted via other known methods to the remote location. The remote physician's display may be configured to display either a view of the patient, a view emulating the technician's display 606, or both. Programmers 601 according to the present invention may also permit various levels of teleconferencing. For example, a second microphone and speaker (not shown) associated with programmer 601 may permit the remote physician to hear and speak with the patient while monitoring the patient via video camera 626. The remote physician may also be able to carry on private conversations with the technician via speaker 611 and microphone 610.

Figures 8, 9:
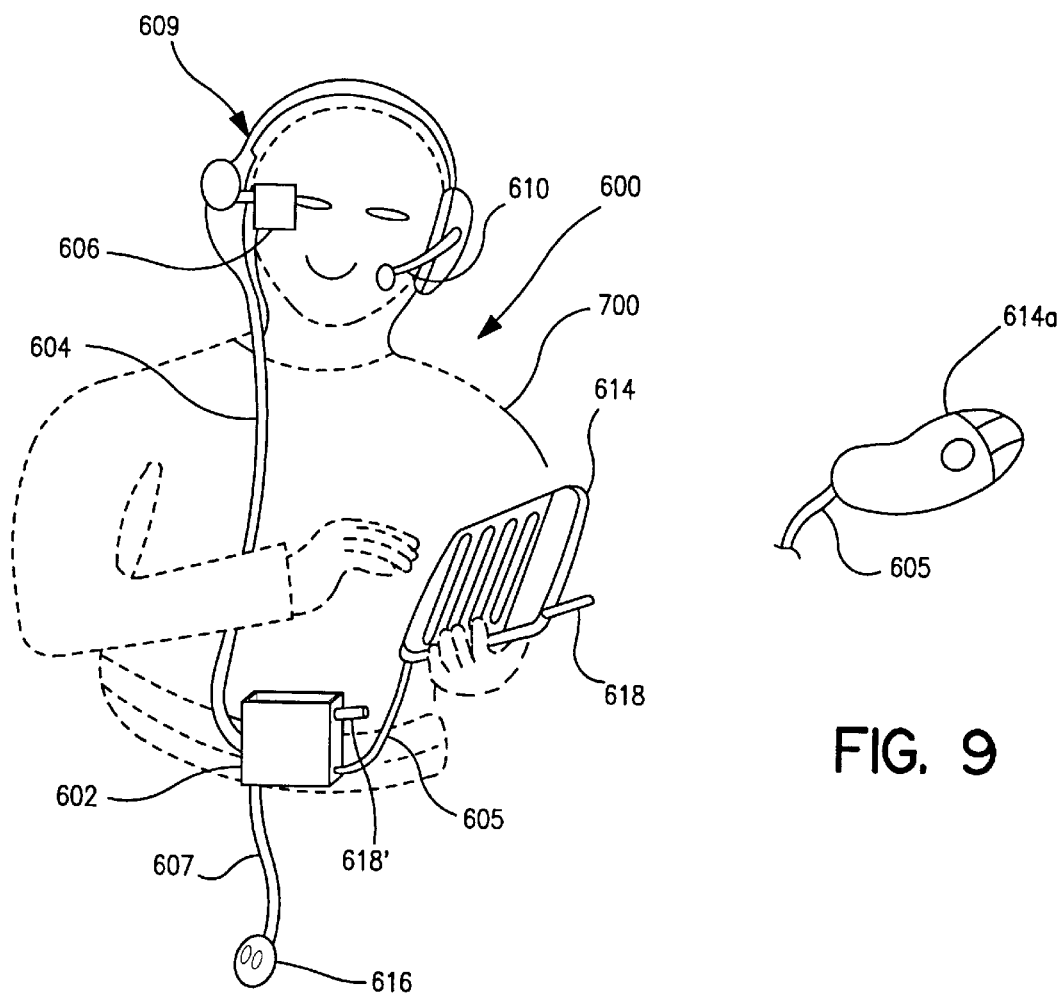
FIG. 8 is a view of a body-worn programmer in accordance with one embodiment of the invention.
FIG. 9 is a view of a trackball input device in accordance with another embodiment of the invention.

FIG. 8 illustrates one embodiment of programmer 601 during operation. Housing 602 is worn on the belt of operator 700. As already described above, housing 602 is coupled to headset apparatus 609, input device 614, and wand 616 by cables 604, 605 and 607, respectively. Display 606 is positioned forward of the head to permit convenient viewing while optional microphone 610 may be positioned in close proximity to the operator's mouth.

The telemetry apparatus 615 (see FIG. 6) may, as also mentioned above, utilize antenna 618 (coupled to keyboard 614) or 618' (coupled to housing 602) in addition to or in lieu of wand 616.

The embodiment illustrated in FIG. 8 utilizes a conventionally-styled keyboard as input device 614. However, other embodiments may replace or augment the keyboard with trackball device 614a as illustrated in FIG. 9. In still other embodiments, voice commands delivered via microphone 610 (see FIG. 8) may be used to control programmer 601.

While described herein with reference to cardiac implants, programming devices and methods in accordance with the present invention may be used in conjunction with other IMDs, e.g., neurologic implants, nerve stimulators, muscle stimulators, or, alternatively, external medical devices, e.g., respiratory monitors, that may incorporate the circuits necessary for communication and operation as described herein. In addition, programmers in accordance with the present invention may be adapted to function not only with IMDs, but also with other medical devices and systems now known and those not yet commercially available.

Advantageously, by making the components of programmer 601 wearable, no cart or desktop is required. As a result, programmer 601 does not impede or displace other equipment or interfere with personnel who may already be attending to the patient. Furthermore, because video display apparatus 606 is head-mounted, it remains conveniently oriented regardless of the operator's line of sight. That is, operator 700 can view display 606 without turning away from the direction of the patient.

The complete disclosure of the patents, patent documents (including patent applications), and publications cited in the Background, Detailed Description and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of IMDs for cardiac therapy but may, as mentioned above, be used with most any medical device, implanted or external. The present invention further includes within its scope methods of making and using the programmers and systems described herein above.

What is claimed is:

1. A programmer system for use in programming an implantable medical device, comprising:

a programmer comprising external programming circuitry;

a headset video display apparatus comprising a video display panel attached to or forming a portion of the apparatus, the headset apparatus being configured to be worn on a head of a user and to support the video display panel in such a position that the user may view the video display panel while the headset apparatus is worn on the user's head, the headset apparatus being operably coupled to the programming circuitry, the headset apparatus being operable under control of the programming circuitry to display to the user at least programming information associated with the implantable medical device;

a data entry device coupled to the programming circuitry; and a telemetry apparatus operable under control of the programming circuitry to communicate with the implantable medical device.

2. The programmer system of claim 1, wherein the data entry device is at least one of a keyboard, a microphone, and a trackball.

3. The programmer system of claim 1, wherein the telemetry apparatus comprises a programming wand for use in communicating with the implantable medical device.

4. The programmer system of claim 1, wherein the telemetry apparatus comprises an antenna affixed to at least one of a housing enclosing the programming circuitry and a housing of the data entry device.

5. The programmer system of claim 1, wherein the headset video display apparatus is further operable to display information to the user regarding one or more of the implantable medical device and the programmer.

6. The programmer system of claim 1, wherein the programming circuitry is enclosed in a body-wearable housing.

7. The programmer system of claim 1, further comprising a speaker coupled to the programming circuitry.

8. A method for programming an implantable medical device, comprising:

providing an implantable medical device, wherein the impfantable medical device includes an implantable medical device telemetry receiver;

providing a programmer system, comprising:

a programmer comprising programming circuitry;

a headset video display apparatus comprising a video display panel attached to or forming a portion of the apparatus, the headset apparatus being configured to be worn on a head of a user and to support the video display panel in such a position that the user may view the video display panel while the headset apparatus is worn on the user's head, the headset apparatus being operably coupled to the programming circuitry, the headset apparatus being operable under control of the programming circuitry to display to the user at least programming information associated with the implantable medical device;

a data entry device coupled to the programming circuitry; and a telemetry apparatus operable under control of the programming circuitry to communicate with the implantable medical device; and programming the implantable medical device with the programming system, wherein programming information is displayed on the headset video display apparatus to the user.

9. The method of claim 8, wherein programming the implantable medical device comprises transmitting programming instructions from the telemetry apparatus to the implantable medical device telemetry receiver.

10. The method of claim 8, wherein programming the implantable medical device further comprises entering programming instructions from a data entry device coupled to the programming circuitry.

11. The method of claim 10, wherein entering programming instructions comprises typing keystrokes on a keyboard.

12. The method of claim 10, wherein entering programming instructions comprises manipulating a trackball.

13. The method of claim 10, wherein entering programming instructions comprises providing voice commands to a microphone.

14. The method of claim 8, wherein the telemetry apparatus comprises a wand for positioning proximate the implantable medical device.

15. The method of claim 8, further comprising transmitting implantable medical device status information from an implantable medical device telemetry transmitter to the telemetry apparatus.

16. The method of claim 15, further comprising transmitting patient data from the implantable medical device telemetry transmitter to the telemetry apparatus.

17. The method of claim 8, wherein the telemetry apparatus comprises an antenna coupled to the programming circuitry and mechanically coupled to at least one of a data entry housing and a housing of the programming circuitry.

18. The method of claim 8, further comprising:

providing a video camera associated with the programmer system;

capturing video data with the video camera; and transmitting the video data to a remote location.

19. A portable apparatus for programming an implantable medical device, the apparatus comprising:

a programmer housing that is wearable on the body, the housing enclosing programming circuitry;

a telemetry apparatus operably coupled to the programming circuitry, the telemetry apparatus being operable to communicate with the implantable medical device; and a headset video display apparatus comprising a video display panel attached to or forming a portion of the headset apparatus, the headset apparatus being configured to be worn on a head of a user and to support the video display panel in such a position that the user may view the video display panel while the headset apparatus is worn on the user's head, the headset apparatus being operably coupled to the programming circuitry and operable to display programming information to the user regarding the implantable medical device.

20. The apparatus of claim 19, further comprising a data entry device operably coupled to the programming circuitry.

21. The apparatus of claim 20, wherein the data entry device is integral with the programmer housing.

22. The apparatus of claim 20, wherein the data entry device is separate from the programmer housing.

23. The apparatus of claim 20, wherein the data entry device is a keyboard.

24. The apparatus of claim 20, wherein the data entry device is a microphone wearable on the body and operable to deliver voice commands to the programming circuitry.

25. The apparatus of claim 20, wherein the telemetry apparatus comprises an antenna coupled to the data entry device.

26. The apparatus of claim 19, wherein the telemetry apparatus comprises a wand for positioning proximate the implantable medical device.

27. The apparatus of claim 19, wherein the telemetry apparatus comprises an antenna affixed to the housing.

28. The apparatus of claim 19, further comprising a video camera and network circuit for transmitting at least a video signal to a remote location.

29. A system for programming an implantable medical device, the system comprising:

an implantable medical device for implantation within a body;

a programmer housing that is wearable on the body;

programming circuitry disposed within the housing;

a telemetry apparatus coupled to the programming circuitry, the telemetry apparatus being operable to communicate with the implantable medical device; and a headset video display apparatus comprising a video display panel attached to or forming a portion of the headset apparatus, the headset apparatus being configured to be worn on a head of a user and to support the video display panel in such a position that the user may view the video display panel while the headset apparatus is worn on the user's head, the headset apparatus being operably coupled to the programming circuitry, the headset video display apparatus being operable to display programming information to the user regarding the implantable medical device.

30. The system of claim 29, wherein the implantable medical device is a cardiac pacing device.

31. The system of claim 30, wherein the implantable medical device is at least one of a pacemaker, cardioverter, or defibrillator.

32. The system of claim 29, further comprising an input device selected from the group consisting of a keyboard, a track ball, and a microphone.

33. The system of claim 29, further comprising a speaker.

34. The system of claim 29, wherein the headset further comprises a speaker.

35. The system of claim 29, wherein the headset further comprises a video camera.

* * * * *

UNITED STATES PATENT AND TRADEMARK OFFICE
CERTIFICATE OF CORRECTION

PATENT NO.   : 6,442,430 B1
DATED        : August 27, 2002
INVENTOR(S)  : Bozidar Ferek-Petric It is certified that error appears in the above-identified patent and that said Letters Patent is hereby corrected as shown below:

Column 14,
Line 65, delete "impfantable" and insert -- implantable --.

Signed and Sealed this

Ninth Day of November, 2004

JON W. DUDAS
*Director of the United States Patent and Trademark Office*